(12) United States Patent
Kanai et al.

(10) Patent No.: US 7,221,456 B2
(45) Date of Patent: May 22, 2007

(54) SURFACE PLASMON RESONANCE SENSOR

(75) Inventors: Naritoshi Kanai, Bunkyo-ku (JP); Isao Shimoyama, Nerima-ku (JP); Kiyoshi Matsumoto, Nakano-ku (JP); Kazunori Hoshino, Shibuya-ku (JP)

(73) Assignee: Aisin Seiki Kabushiki Kaisha, Kariya-shi (JP)

( * ) Notice: Subject to any disclaimer, the term of this patent is extended or adjusted under 35 U.S.C. 154(b) by 393 days.

(21) Appl. No.: 10/995,368

(22) Filed: Nov. 24, 2004

(65) Prior Publication Data
US 2005/0117158 A1  Jun. 2, 2005

(30) Foreign Application Priority Data
Nov. 27, 2003  (JP)  ............................. 2003-396965

(51) Int. Cl.
*G01N 21/22* (2006.01)

(52) U.S. Cl. ...................................... 356/445

(58) Field of Classification Search ...................... None
See application file for complete search history.

(56) References Cited

U.S. PATENT DOCUMENTS

| | | |
|---|---|---|
| 5,912,456 A | 6/1999 | Melendez et al. |
| 6,111,248 A | 8/2000 | Melendez et al. |
| 6,424,418 B2 * | 7/2002 | Kawabata et al. .......... 356/445 |
| 6,462,809 B1 * | 10/2002 | Ryan et al. .................. 356/128 |
| 6,507,402 B2 | 1/2003 | Negami et al. |
| 6,594,018 B1 | 7/2003 | Bartholomew |
| 6,738,141 B1 * | 5/2004 | Thirstrup ..................... 356/445 |
| 2003/0048452 A1 * | 3/2003 | Johansen ..................... 356/445 |
| 2004/0130723 A1 * | 7/2004 | Yager et al. ................. 356/445 |
| 2007/0008546 A1 * | 1/2007 | Ho et al. ..................... 356/481 |
| 2007/0013912 A1 * | 1/2007 | Ivarsson ..................... 356/445 |

FOREIGN PATENT DOCUMENTS

| | | |
|---|---|---|
| JP | 10-19768 | 1/1998 |
| JP | 11-344437 | 12/1999 |

OTHER PUBLICATIONS

K. Nagata, et al., "Real-Time Analysis of Biomoleculer Interactions", Ed. Springer-Verlag Tokyo, pp. 22-23.

* cited by examiner

*Primary Examiner*—Michael P. Stafira
(74) *Attorney, Agent, or Firm*—Oblon, Spivak, McClelland, Maier & Neustadt, P.C.

(57) ABSTRACT

A surface plasmon resonance sensor comprises a prism having parallel surfaces, a light source provided on one surface of the prism, a detecting means provided on the same surface where the light source is provided, a metal thin film provided on the other surface of the prism, and at least one of light absorbing members provided in the prism for blocking light emitted from the light source at any angle except a predetermined angle so that the metal thin film is illuminated by the light emitted from the light source at the predetermined angle, and such light is totally reflected at the metal thin film so as to reach the detecting means.

19 Claims, 4 Drawing Sheets

SURFACE PLASMON RESONANCE SENSOR

CROSS REFERENCE TO RELATED APPLICATIONS

This application is based on and claims priority under 35 U.S.C. § 119 to Japanese Patent Application 2003-396965, filed on Nov. 27, 2003, the entire content of which is incorporated herein by reference.

FIELD OF THE INVENTION

This invention generally relates to a surface plasmon resonance sensor for qualitative measuring and quantitative measuring of detecting substance as a target.

BACKGROUND

Surface plasmon resonance (hereinafter referred to as SPR) sensor is a measuring device which monitors the interaction of biomolecular on a surface of the sensor chip on the molecular level. One molecule is immobilized on the surface of the sensor chip, and sample solution including another molecule which interacts with the immobilized molecule is provided on the surface of the sensor chip though a microchannel. SPR signal reflecting a slight amount of refraction index gradient near the sensor chip surface resulting from the association or dissociation of the aforementioned interacting molecules is detected.

The gradient with time of the signals are monitored in real-time and displayed as a time course in a graph so called a sensorgram. Thus, as monitoring the interaction of such molecules on the surface of the sensor chip in real-time as the interaction occurs, the target (e.g. micro-substance) specifically associate relative to the surface of the sensor chip.

Different methods of such measuring device using SPR depending on the optical alignment have been disclosed. One measuring device is described in *Real-Time Analysis of Biomolecular Interactions*, K. Nagata, H. Handa, P22, Ed. Springer-Verlag Tokyo. In addition, another measuring device using a small SPR sensor disclosed in JP1019768A and JP11344437A.

FIG. 6 illustrates a diagram indicating a structure of the sensor disclosed in JP1019768A. A sensor 100 includes a substrate 101 and a light source 102 provided thereon. A light 110 emitted from the light source into a housing 103 is polarized at a polarizer 104. Further, the light 110 is reflected at a SPR film 105 and reflected at a flat mirror 106. Finally, the light 110 reaches a detector array 107.

FIG. 7 illustrates a diagram indicating a structure of the sensor disclosed in JP11344437A. A sensor 200 includes a surface emitting laser 202, a one-dimentional CCD sensor array 203 and a Si substrate 201. The surface emitting laser 202 and the one-dimensional CCD sensor array 203 are arranged on the Si substrate 201 along a line extending in horizontal direction in FIG. 7. To maintain its mechanical strength, the Si substrate 201 is supported by an insulating substrate 204. Terminals 205 are drawn from the insulating substrate 204 to drive the surface emitting laser 202 and take out signals from the CCD sensor array 203. A cylindrical lens 206 is provided above the surface emitting laser 201 to expand the laser light in the arrangement direction of the CCD sensor array 203. These elements are molded with a light-transmitting polymethylmethacrylate resin 207 to construct a sensor apparatus. The expanded laser light is totally reflected by an outer surface of a metal thin film 208, and the focal length of the cylindrical lenses 206 is set such that the intensity of the totally-reflected light can be measured by the CCD sensor array 203 corresponding to its incident angle.

If the light is emitted from the light source provided separately from the sensor, a optical axis may be misaligned due to vibration so as to disenable the measurement. The aforementioned sensors 100 and 200 integrally include the sensor elements such as the metal thin film, the light source and the detector so as to improve the shockproof, however; the sensors 100 and 200 are not configured for seeking the portability. Specifically, the sensors 100 and 200 have complicated structures and less durability in a shaken condition. Further, the sensors 100 and 200 include such complicated structures and the detector array 107 and 203, so that microminiaturization of the sensor has been difficult.

Thus, a need exists for the SPR sensor to have high shockproof and durability, or to microminiaturize the SPR sensor.

SUMMARY OF THE INVENTION

According to an aspect of the present invention, a surface plasmon resonance sensor comprises a prism having parallel surfaces, a light source provided on one surface of the prism, a detecting means provided on the same surface where the light source is provided, a metal thin film provided on the other surface of the prism, and at least one of light absorbing members provided in the prism for blocking light emitted from the light source at any angle except a predetermined angle so that the metal thin film is illuminated by the light emitted from the light source at the predetermined angle, and such light is totally reflected at the metal thin film so as to reach the detecting means.

According to another aspect of the present invention, a surface plasmon resonance sensor comprises a semiconductor silicon substrate as a prism, a light source formed on one surface of the semiconductor silicon substrate and including an organic EL element or a light emitting diode for emitting light which transmits through the semiconductor silicon substrate toward at least the other surface of the semiconductor silicon substrate facing to the one surface thereof, a metal thin film formed at the other surface of the semiconductor silicon substrate to be illuminated by the light emitted from the light source and transmitting through the semiconductor silicon substrates, a photodiode formed on the one surface of the semiconductor silicon substrate by doping for receiving the light emitted from the light source and totally reflected at an interface between the semiconductor silicon substrate and the metal thin film, and a first light path formed in the semiconductor silicon substrate so that only the light emitted from the light source at a predetermined angle reaches the metal thin film.

BRIEF DESCRIPTION OF THE DRAWINGS

The foregoing and additional features and characteristics of the present invention will become more apparent from the following detailed description considered with reference to the accompanying drawings, wherein.

DETAILED DESCRIPTION

An embodiment of the present invention will be explained hereinbelow referring to attached drawings.

Figure 1:
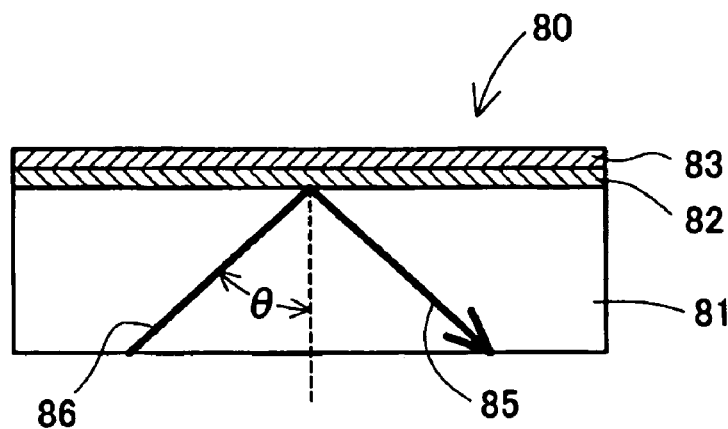
FIG. 1 illustrates a simplified diagram of a part of a surface plasmon resonance sensor.

First, a structure and principle of a surface plasmon resonance (hereinbelow referred to as SPR) sensor will be explained. FIG. 1 illustrates a partially simplified diagram of the SPR sensor. The SPR sensor 80 includes a prism 81 over which a gold thin film 82 is provided. It is preferred to use a certain kind of metal such as gold or silver is needed to resonate the surface plasmon. Generally, a gold thin film is used on the SPR sensor because of its chemically inertness or high efficiency to generate the SPR signal. Binding substance such as a ligand or a molecular recognition element is applied on the metal thin film such as the gold thin film so as to specifically interact and bind with a specific detection species.

As shown in FIG. 1, an incident light 86 is applied to the SPR sensor 80 at angle θ, and the intensity of a reflected light 85 reflected at and an interface between the prism 81 and the gold thin film 82 is measured. A measuring device using such SPR sensor 80 includes a light source such as a laser diode and a receiving means such as a photodiode array (not shown). In this configuration, the incident light 86 is emitted from the light source totally reflected at the interface between the prism 81 and the gold thin film 82. Finally, the total-reflected light 85 is received by the receiving means to detect the intensity of the total-reflected light 85.

Evanescent wave is generated at the gold thin film 82 side of the interface between the gold thin film 82 and the prism 81 when the interface between the prism 81 and the gold thin film 82 is illuminated by the light emitted from the light source to be totally reflected at the interface. When the frequency of the surface plasmon wave on the surface of the gold thin film 82 becomes equal to the frequency of the evanescent wave at a specific incident angle, the resonance phenomena takes place, as a result, the surface plasmon is excited. Once the surface plasmon is excited, a part of the energy of the incident light is used for the SPR, as a result, the intensity of the reflected light 85 is significantly reduced.

Figure 2:
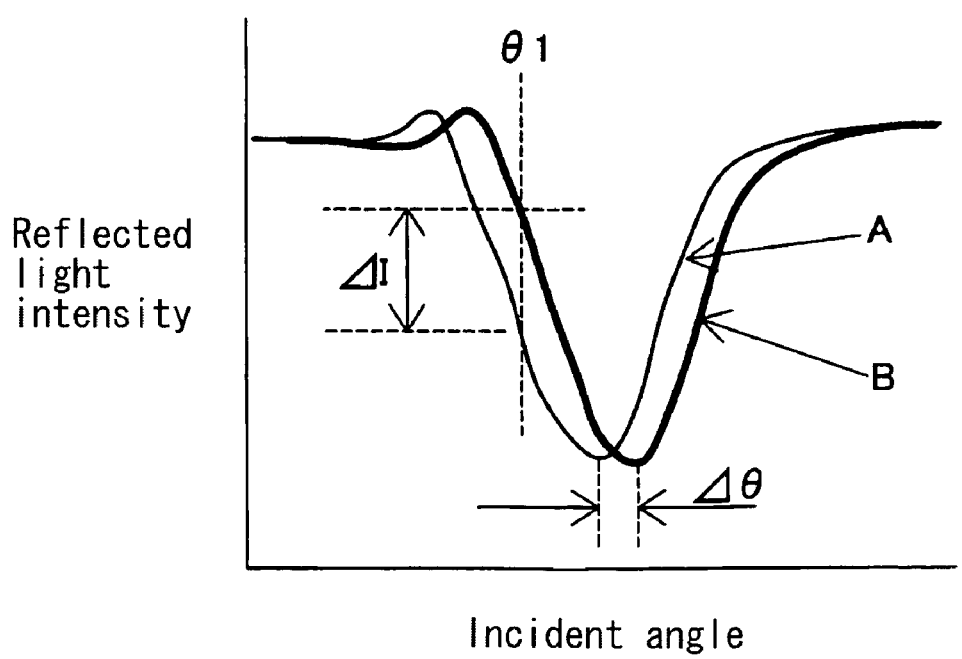
FIG. 2 illustrates a graph indicating dependence on the incident angle of intensity of reflected light.

A graph in FIG. 2 shows dependence on incident angle of the reflected light intensity detected by the SPR sensor. Reduction of the intensity of the reflected light 85, so called a valley of light, is recognized at the specific incident angle, and such optical phenomenon is the SPR. The SPR depends on the wavelength and the angle of the incident light. When the SPR is generated, the energy of the light including a specific incident angle or a specific wavelength is used to generate the SPR. Thus, the intensity of the reflected light having a corresponding reflected angle or the wavelength is reduced.

The SPR also depends on a refractive index near the surface of the metal layer. Thus, in accordance with the change of the refractive index, the resonance angle is changed when the wavelength is constant, and the resonance wavelength is changed when the incident angle is constant.

Specifically, the refractive index near the surface of the metal layer can be analyzed by monitoring the resonance angle or the resonance wavelength based on the intensity of the reflected light. Thus, when the refractive index of the surface of the gold thin film 82 is changed, and the resonance angel is shifted from A in FIG. 2 to B in FIG. 2, qualitative information and quantitative information of the sample solution can be obtained by detecting the chronological change of the shift amount. In the SPR sensor of the embodiment according to the present invention, the incident angle is settled at, for example, θ1 in FIG. 2, and the qualitative information and the quantitative information of a target in the sample solution are measured from change ΔI of the intensity of the shifted reflected light.

Figure 3:
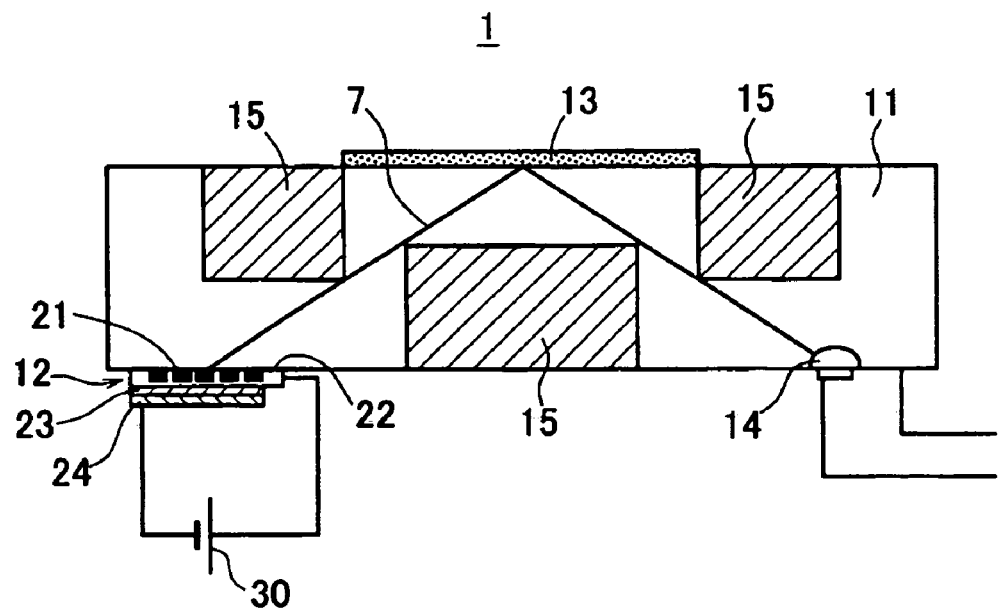
FIG. 3 illustrates a cross section of a embodiment of the surface plasmon resonance sensor according to the present invention.

The SPR sensor of the embodiment according to the present invention will be specifically explained. FIG. 3 illustrates a cross sectional view of the SPR sensor of the embodiment according to the present invention. The SPR sensor 1 includes a prism 11, a light source 12, a detector 14 and a metal thin film 13. The prism 11 has parallel surfaces on the upper and lower side thereof, and the light source 12 and the detector 14 are provided on one surface of the prism 11, and the metal thin film 13 is provided on the other surface of the prism 11. Thus, the metal thin film 13 is illuminated by light 7 emitted from the light source 12 through the prism 11. Further, the light 7 is totally reflected at the metal thin film 13 and the reflected light is received by the detector 14. In the embodiment according to the present invention, the target is detected by the method for detecting the light intensity, thus the incident angle of the light 7 relative to the metal thin film 13 needs to be settled at θ1. Thus, the SPR sensor 1 has a configuration where the metal thin film 13 is illuminated by only the light 7 whose angle is at θ1 emitted from the light source 12. Specifically, light absorption blocks 15 are provided for absorbing the diffusing light emitted from the light source 12 whose angle is not at θ1.

The SPR sensor 1 according to the embodiment employs a semiconductor silicon substrate as the prism 11 so as to microminiaturize the sensor. The prism 11 is 300-1000 μm in thickness and 2-5 mm in horizontal and vertical lengths. Thus, since the semiconductor silicon substrate is employed as the prism 11, the SPR sensor 1 can be manufactured in a semiconductor manufacturing process.

Again, to excite the SPR, the light from the light source 13 should be transmitted through the prism 11. In this point of view, when the semiconductor silicon substrate is used as the prism 11, it matters what kind of the light source is used because the semiconductor silicon substrate prevent some kind of light, such as visible light, from passing therethrough. In the embodiment according to the present invention, element for emitting infrared radiation is used as the light source 12 such as an organic compound electroluminescence (hereinbelow referred to as organic EL) element or a light emitting diode. In addition, the SPR sensor 1 employs a photodiode as the detector 14 which is mountable on the semiconductor silicon substrate in the semiconductor manufacturing process.

A manufacturing process of the SPR sensor 1 will be briefly explained below. On one side of the prism (hereinafter referred to as "semiconductor silicon substrate") 11, the detector (hereinafter referred to as "photodiode") 14 is formed by doping. The light source (hereinbelow referred to as "organic EL element") 12 is also formed on the same surface where the detector 14 is formed. A slit pattern 21 is formed on the organic EL element with aluminium by deposition so that the metal thin film 13 is illuminated by only the light whose polarizing direction is P-polarized light. Specifically, only the P-polarized light has influence on the SPR, so that the slit pattern 21 is provided for enhancing detecting sensitivity by receiving only the P-polarized light at the photodiode 14. Although the detecting sensitivity may be declined, the intensity of the light can be measured without the slit pattern 21. In other words, the slid pattern 21 is not an essential element.

A thin insulating film (not shown) is formed on the slit pattern 21, and a transparent conducting layer made of ITO (Indium Tin Oxide) is formed in a predetermined pattern shape on the insulating film as an anode 22 as a first electrode. Further, an organic layer 23 made of a thin film of organic compound material including a luminescent layer on the anode 22. As aforementioned above, since infrared light would transmit through the semiconductor silicon substrate 11, the organic layer 23 is made of luminescent molecule which emits infrared light. On the organic layer 23, a cathode 2 for a second electrode made of aluminium is formed by deposition in a predetermined pattern. The anode 22 and the cathode 24 are wired and a power source 30 is provided therebetween.

Further, a light path (first light path) is formed in the semiconductor silicon substrate 11 so that the metal thin film 13 is illuminated by only the light 7 emitted from the organic EL element 12 at incident angle $\theta 1$ so as to excite the SPR and reaches the photodiode 14 after totally reflected at the metal thin film 13. Specifically, light absorbing blocks 15 are formed in the semiconductor silicon substrate 11 so as to block any paths of light emitted from the organic EL element 12 except the path of the light 7 at incident angle $\theta 1$. Further, a light path (second light path) is formed in the semiconductor silicon substrate 11 so that only the light reflected at the metal thin film 13 at a predetermined angle reaches the photodiode 14. Each light absorbing block 15 is formed by filling the grooves formed on each surface of the semiconductor silicon substrate by etching method with infrared light absorbing material.

Finally, the gold thin film as the metal thin film 13 is deposited on the surface of the semiconductor silicon substrate 11 where the organic EL element 12 is not formed. It is preferred to use the gold thin film because a certain kind of metal such as gold or silver is needed to resonate the SP. Generally, gold thin film is used because of its chemically inertness or high efficiency to generate the SPR signal. In addition, binding substance such as a ligand or a molecule recognition element is applied on the metal thin film such as the gold thin film so as to specifically interact and bind with a specific detection species.

The metal thin film 13 is alternatively attached on the surface of the semiconductor silicon substrate 11 where the organic EL element 12 is not formed. Specifically, the metal thin film 13 is provided on the surface of a thin glass substrate, and then one surface of the glass substrate where the metal thin film 13 is not provided is contacted with the surface of the semiconductor silicon where the organic EL element 12 is not formed. Finally, the glass substrate is attached on the surface of the semiconductor silicon substrate. In this configuration, oil may be applied at the contacting portion between the glass substrate and the semiconductor silicon substrate so as to prevent air from interfusing into the contacting portion.

Behavior of the SPR sensor 1 of the embodiment having the aforementioned configuration will be explained hereinbelow. The SPR sensor 11 is conducted by the power source 30 connected to the anode 22 and the cathode 24 of the organic EL element. Voltage is applied to the organic layer 23 so that the organic layer 23 emits light. The light emitted from the organic layer 23 is transmitted through the anode 22 made of a transparent electrode ITO. At this point, only the light whose polarizing direction is P-polarized light is selected due to the slit pattern 21. Further, the light emitted from the organic layer 23 is infrared light so that the P-polarized infrared light enters the semiconductor silicon substrate.

The light emitted from the organic EL element 12 is diffused inside the semiconductor silicon substrate, however, the metal thin film 13 is illuminated by only the light 7, one of these diffused lights, at incident angle $\theta 1$ without being blocked by the light absorbing blocks 15. Further, the light 7 reflected at the metal thin film 13 is received by the photodiode 14 formed on the same surface of the semiconductor silicon substrate where the organic EL element 12 is formed. When the refraction index is changed near the surface of the metal thin film 13, the intensity of the reflected light received by the photodiode 14 is changed. Once the reflected light is received by the photodiode 14, voltage in proportion to the intensity of the reflected light is outputted from the photodiode 14 as a measuring signal. Thus, the change of the refraction index near the metal thin film 13 can be detected by measuring the change of the measuring signal outputted from the photodiode.

The measuring signal outputted from the photodiode 14 is sent to an arithmetic processing unit (not shown). The qualitative information and the quantitative information based on the measuring signal are analyzed based on the change $\Delta I$ of the intensity of the reflected light. The path of the light 7 at incident angle $\theta 1$ is formed by providing the light absorbing blocks 15 as shown in FIG. 2 so as to obtain the information of the intensity of the reflected light at incident angle $\theta 1$. Thus, when the refraction index is changed based on whether or not the target exist at the metal thin film 13, and the resonance angle is changed at $\Delta \theta$, the intensity of the reflected light at the resonance angle $\theta 1$ is changed at $\Delta I$. Thus, the change $\Delta I$ can be detected by monitoring the measuring signal; as a result, the qualitative information and the quantitative information of the target can be obtained.

While such measuring operation is conducted, a part of the light emitted from the organic EL element 12 whose incident angle is not at the incident angle $\theta 1$ may not be blocked and absorbed by the light absorbing blocks 15. Such light can be absorbed by the light absorbing blocks 15 on the way to the photodiode 14. Even if the light whose incident angle is not $\theta 1$ is not fully absorbed by the light absorbing blocks 15, the intensity of such light becomes very small so as to be ignored as noise.

As aforementioned before, the SPR sensor 1 including the power source and the receiving portion is a micromini chip-type sensor is formed in semiconductor process. As a usage of such SPR sensor, a screw 5 at which the SPR sensor 1 is mounted can be proposed. Specifically, the SPR sensor 1 is attached at the top end of the screw 5 exposing the metal thin film 13 side. The wiring of the organic EL element 12 and the wire of the photodiode 14 through which the signal is transmitted are come out from the head portion of the screw 5. Such screw 5 may be, for example, screwed at the cover of a battery box so as to be immersed in electrolyte of the battery. Further, the SPR sensor 1 may be mounted at the top end of a measuring stick for measuring the amount of the engine oil.

The semiconductor silicon substrate 11 of the SPR sensor 1 according to the embodiment integrally includes not only the organic EL element 12 as the light source but also the metal thin film 13 and the photodiode 14 so that the incident angle θ1 of the light 7 is not misaligned even if vibration if applied to the SPR sensor 1. Thus, such sensor is portable and mountable to a movable body such as a vehicle. Unless the position of each light absorbing block 15 is moved, the incident angle θ1 is stable so as to enhance portability and durability of the sensor.

Figure 5:
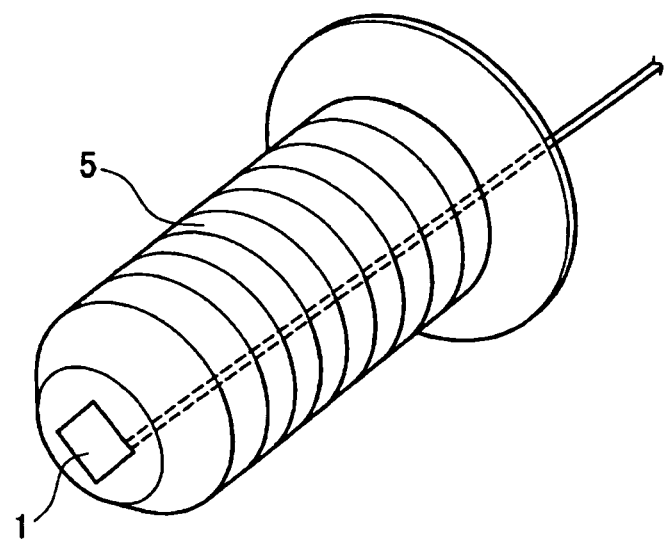
FIG. 5 illustrates a diagram indicating a usage of the surface plasmon resonance sensor of the embodiment according to the present invention.
Figure 6:
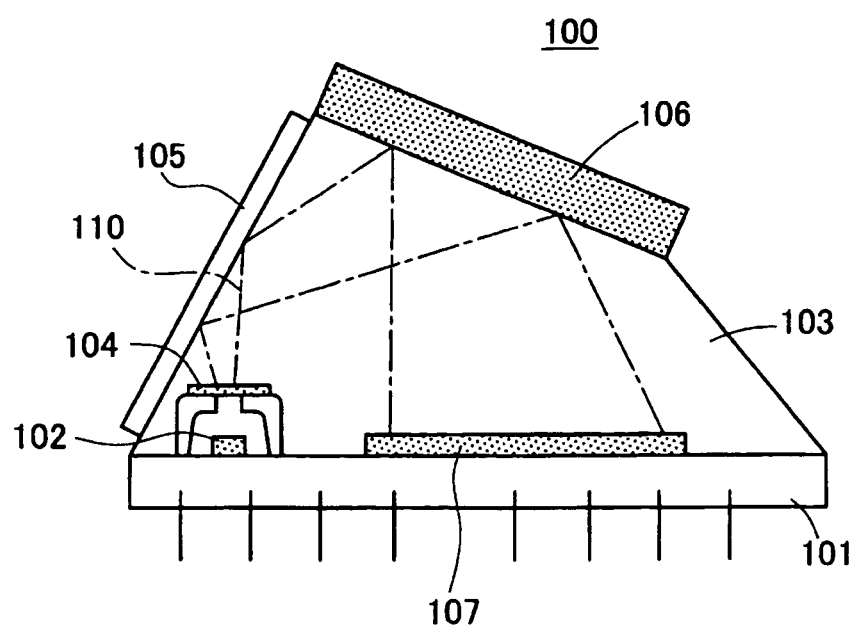
FIG. 6 illustrates a diagram indicating a structure of a sensor disclosed in JP1019768A.
Figure 7:
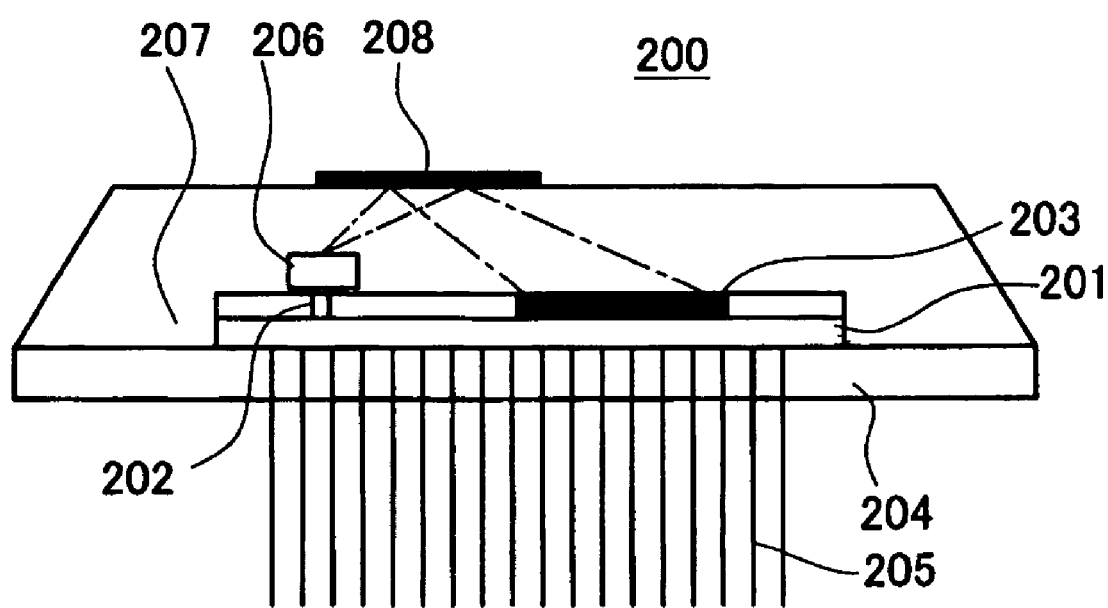
FIG. 7 illustrates a diagram indicating a structure of a sensor disclosed in JP11344437A.

In addition, the thickness of the SPR sensor 1 according to the embodiment is 300-1000 µm and the horizontal and vertical lengths are 2-5 mm. such microminiature sensor can be applied at the top end of the screw 5 as shown in FIG. 5 so as to be easily mounted to various measuring objects such as a vehicle battery or a vehicle engine. Thus, operations which have been manually and periodically carried by human such as measuring and monitoring operation can be constantly and automatically examined with the SPR sensor 1.

Further, the semiconductor silicon substrate 11 as a prism integrally includes the organic EL element 12 as a light source and the photodiode 14 as a receiving element so that the incident angle of the light is stable. In addition, such simple configuration enhances the durability of the sensor.

The photodiode 14 is formed on the semiconductor silicon substrate 11 by doping so that the SPR sensor 1 can be manufactured with semiconductor manufacturing technique, as a result, the production cost of the sensor can be remarkably reduced. Specifically, a plurality of sensor can be mounted to the vehicle without increasing the vehicle manufacturing cost.

Figure 4:
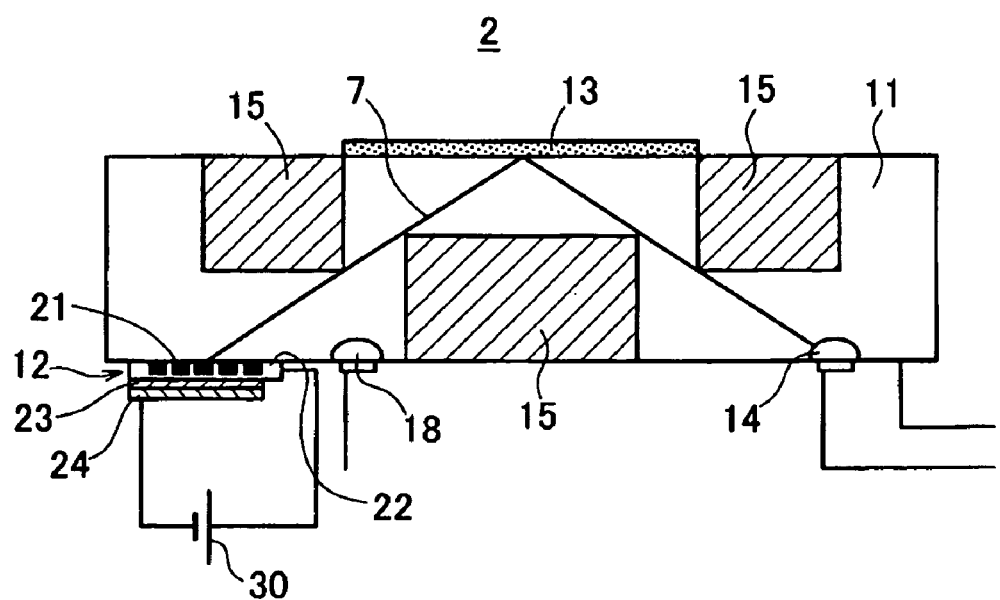
FIG. 4 illustrates a cross section of another embodiment of the surface plasmon resonance sensor according to the present invention.

Another embodiment according to the present invention will be explained in accordance with FIG. 4. A SPR sensor 2 shown in FIG. 4 having a same configuration as the SPR sensor 1 has includes a photodiode 18 on the side where the organic EL element 12 is provided for directly receiving the light emitted from the organic EL element 12. Comparing the intensity of the light received at the photodiode 18 and the light received at the photodiode 14, variation of the light emitting amount due to environmental variation such as temperature change and the change of the sensitivity of the photodiode 14 can be eliminated. Thus, reliability of the sensor can be increased.

A transistor can be alternatively used as a detector for receiving the infrared light. In this case, the prism may be made of glass, and the organic EL element is attached as a light source, however, a light emitting diode (LED) emitting infrared light may be used as the light source.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the sprit of the present invention. Accordingly, it is expressly intended that all such variations, changes and equivalents which fall within the spirit and scope of the present invention as defined in the claims, be embraced thereby.

The invention claimed is:

1. A surface plasmon resonance sensor comprising:
a prism having parallel surfaces;
a light source provided on one surface of the prism;
a detecting means provided on the same surface where the light source is provided;
a metal thin film provided on the other surface of the prism, and
at least one of light absorbing members provided in the prism for blocking light emitted from the light source at any angle except a predetermined angle so that the metal thin film is illuminated by the light emitted from the light source at the predetermined angle, and such light is totally reflected at the metal thin film so as to reach the detecting means.

2. A surface plasmon resonance sensor according to claim 1, wherein the prism includes a semiconductor silicon substrate, the light source includes an organic EL element or a light emitting diode which emits infrared light, and the detecting means includes a photodiode.

3. A surface plasmon resonance sensor according to claim 2, wherein the photodiode is formed by doping on the one surface of the semiconductor silicon substrate; the organic EL element includes an anode made of a transparent conductive film and formed in a predetermined pattern form, an organic layer formed on the anode and made of a thin film of organic compound material including a light emitting molecule for emitting infrared light and a cathode formed on the organic layer by deposition in a predetermined pattern form; a gold thin film as the metal thin film is deposited on the other surface of the semiconductor silicon substrate; and a groove formed by etching on the semiconductor silicon substrate is filled with the light absorbing member.

4. A surface plasmon resonance sensor according to claim 1, wherein a polarizing means is provided between the prism and the light source so that the metal thin film is illuminated by only the light whose polarizing direction is P-polarized emitted form the light source to the prism.

5. A surface plasmon resonance sensor according to claim 2, wherein a polarizing means is provided between the prism and the light source so that the metal thin film is illuminated by only the light whose polarizing direction is P-polarized emitted form the light source to the prism of the semiconductor silicon substrate.

6. A surface plasmon resonance sensor according to claim 3, wherein a polarizing means is provided between the prism and the light source so that the metal thin film is illuminated by only the light whose polarizing direction is P-polarized emitted form the light source to the prism of the semiconductor silicon substrate.

7. A surface plasmon resonance sensor according to claim 4, wherein the polarizing means is including a metallic slit pattern formed by deposition.

8. A surface plasmon resonance sensor according to claim 5, wherein the polarizing means is including a metallic slit pattern formed by deposition.

9. A surface plasmon resonance sensor according to claim 6, wherein the polarizing means is including a metallic slit pattern formed by deposition.

10. A surface plasmon resonance sensor comprising:
a semiconductor silicon substrate as a prism;
a light source formed on one surface of the semiconductor silicon substrate and including an organic EL element or a light emitting diode for emitting light which transmits through the semiconductor silicon substrate toward at least the other surface of the semiconductor silicon substrate facing to the one surface thereof;
a metal thin film formed at the other surface of the semiconductor silicon substrate to be illuminated by the light emitted from the light source and transmitting through the semiconductor silicon substrates;

a photodiode formed on the one surface of the semiconductor silicon substrate by doping for receiving the light emitted from the light source and totally reflected at an interface between the semiconductor silicon substrate and the metal thin film, and a first light path formed in the semiconductor silicon substrate so that only the light emitted from the light source at a predetermined angle reaches the metal thin film.

11. A surface plasmon resonance sensor according to claim 10, wherein the first light path is formed by providing a light absorbing member in the semiconductor silicon substrate for blocking the light emitted from the light source at any angle except at the predetermined angle.

12. A surface plasmon resonance sensor according to claim 10, wherein a second light path is formed in the semiconductor silicon substrate so that only the light reflected at the metal thin film at a predetermined angle reaches the photodiode.

13. A surface plasmon resonance sensor according to claim 12, wherein the second light path is formed by providing a light absorbing member in the semiconductor silicon substrate for blocking the light reflected at the metal thin film at any angle except at the predetermined angle.

14. A surface plasmon resonance sensor according to claim 11, wherein the first light path is formed by filling a groove formed by etching with the light absorbing member.

15. A surface plasmon resonance sensor according to claim 13, wherein the second light path is formed by filling a groove formed by etching with the light absorbing member.

16. A surface plasmon resonance sensor according to claim 10, wherein the light source includes a first electrode made of a transparent conductive film formed on the one surface of the semiconductor silicon substrate in a predetermined pattern form, an organic layer formed on the first electrode and made of a thin film of organic compound material including emission molecule emitting infrared light and a second electrode formed on the organic layer in a predetermined pattern form.

17. A surface plasmon resonance sensor according to claim 16, wherein the transparent conductive film includes an ITO transparent conductive film.

18. A surface plasmon resonance sensor according to claim 10, wherein a polarizing means is provided between the semiconductor silicon substrate and the light source so that the metal thin film is illuminated by only the light whose polarizing direction is P-polarized emitted form the light source to the prism of the semiconductor silicon substrate.

19. A surface plasmon resonance sensor according to claim 18, the polarizing means including a metallic slit pattern is formed by deposition.

* * * * *